(12) United States Patent
Suchy et al.

(10) Patent No.: US 7,578,785 B2
(45) Date of Patent: Aug. 25, 2009

(54) DEVICE FOR EXTENDING ELONGATE BODY PARTS

(75) Inventors: Matthias Suchy, Berlin (DE); Sylvia Suchy, Berlin (DE)

(73) Assignee: MSP Concept GmbH & Co. KG, Berlin (DE)

( * ) Notice: Subject to any disclaimer, the term of this patent is extended or adjusted under 35 U.S.C. 154(b) by 722 days.

(21) Appl. No.: 10/506,640

(22) PCT Filed: Mar. 6, 2003

(86) PCT No.: PCT/DE03/00812

§ 371 (c)(1),
(2), (4) Date: Sep. 3, 2004

(87) PCT Pub. No.: WO03/073967

PCT Pub. Date: Sep. 12, 2003

(65) Prior Publication Data

US 2005/0124854 A1    Jun. 9, 2005

(30) Foreign Application Priority Data

Mar. 7, 2002   (DE) .............................. 202 03 927 U

(51) Int. Cl.
*A61F 5/00* (2006.01)

(52) U.S. Cl. ...................................................... 600/38
(58) Field of Classification Search .............. 600/38–41; 602/32–36, 38–40; 403/397; 24/336, 339
See application file for complete search history.

(56) References Cited

U.S. PATENT DOCUMENTS 5,642,557 A     7/1997   Clews

FOREIGN PATENT DOCUMENTS

| DE | 196 18 352 A1 | 11/1997 |
| DE | 295 21 655 U1 | 6/1998 |
| WO | WO96/26691 | 9/1996 |
| WO | WO97/28764 | 8/1997 |

*Primary Examiner*—John P Lacyk
(74) *Attorney, Agent, or Firm*—The Webb Law Firm

(57) ABSTRACT

A stretching device for permanently extending elongate body parts, comprising stretch rods coupled to a support ring with fixing means which are retained on the distal end thereof. The fixing means consists of a fully or partially elastic, substantially cylindrical component which surrounds the body part and is provided with retaining clips on the outer edge which engage with the stretch rods and which are embodied in the form of slotted hollow cylinders provided with a stop plate. The fixing part is used to fix the body part in a secure and careful manner and can be easily joined to or removed from the stretch rod without overstretching.

19 Claims, 3 Drawing Sheets

DEVICE FOR EXTENDING ELONGATE BODY PARTS

BACKGROUND OF THE INVENTION

The invention relates to a device for permanently extending elongate body parts, particularly the penis, comprising a support ring, at least one stretching rod coupled to the support ring and spring-mounted in axial direction that can gradually be adjusted in length, and fixing means retained on the distal end of the stretching rod.

DESCRIPTION OF THE RELATED ART

Such stretching devices that can help to achieve a permanent expansion of specific body parts such as the penis based on continuously stretching the tissue by applying a stretching force and without the need for surgical intervention are known. For example, DE 196 18 351 A1 describes a device for penis expansion comprising telescopically guided stretching rods that can be locked at the required length. The fixing means on the distal end of the stretching rod is a receiving shell with a support strap that can be set at variable perimeters. This device has a disadvantage in that the stretching force is neither gradual nor can its increase be fine-metered and in that the strap-type fixing of the penis poses risks of injury from using the device.

In another embodiment of a penis expansion device according to DE 295 21 655 U1, the stretching rod is formed by two tapped bushes connected by a threaded rod. This makes fine-metering of the stretching force or the length of the stretching rods possible. In addition, the stretching rods can be pivoted and are spring-mounted in the support ring. The fixing means is a wide strap that surrounds the penis and has two cylindrical pockets spaced to receive the stretching rods. In addition to the risk of injury the strap-type fixing poses, putting on the device is difficult and requires considerable dexterity.

Yet another known stretching device features two parallel threaded rods coupled to the support ring each of which is screwed into a tapped adjustment bush. A spring cover with an internal spring is mounted on the adjustment bush and can be moved telescopically against the spring action. The spring covers can be extended using extension rods. The fixing means for the distal end of the penis is a receiving shell with lateral bushes for plug-in connection of the free ends of the spring covers or extension rods and an elastic fastening strap whose ends can be locked at variable positions in the receiving shell. This device has the disadvantages of requiring a high degree of dexterity and can result in injury due to the elastic fastening strap.

It is the problem of the invention to design a device of the type mentioned above in such a way that simple, convenient, and painless handling of the expansion device is ensured when putting the device on and during its permanent use.

SUMMARY OF THE INVENTION

One important characteristic of the invention is that the fixing means is designed as a preformed cylindrical element that elastically encompasses the respective body part in part or fully. The body part is flexibly supported in stretched condition in a large area around its entire perimeter. High user comfort is ensured due to large-area elastic pressure. Risk of injury by pinching is considerably reduced due to the approximately cylindrical design.

According to another important characteristic of the invention, retaining clips that can be locked into the side of the stretching rod and, in a preferred embodiment, flexibly encompass its perimeter are mounted to the perimeter of the fixing means. This means that the fixing means can be conveniently attached to the penis and only has to be interlocked on the stretching rods with the retaining clip. This simplifies application of the expansion device considerably without the risk of pinching or overstretching the body part. In addition, the stretching device can be temporarily released and re-attached quickly.

According to another important characteristic of the invention, the retaining clips are mounted to the upper rim of the fixing means when viewed in stretching direction, which makes it possible to accommodate shorter body parts.

In one embodiment of the invention, the fixing means encompasses a rigid receiving shell to which retaining clips are formed and a stretching element comprising a domed flexible support part and stretching straps running from its sides that can be locked into slots of the receiving shell.

According to another embodiment of the invention, the receiving shell is also made of a flexible material, or the receiving shell and/or the stretching element have a flexible air-cushion design. The substantially cylindrical fixing means preferably consists of two linked shells with an inflatable air-cushion ring or an elastic material covering their inner surfaces and a lock that closes the shells at variable widths. In this way, the respective body part can be placed and fixed fast and gently in the fixing means as well as released easily and quickly, if required.

In a preferred embodiment, the air cushion ring can be inflated manually or with a compressed air cartridge. A manual pump may be integrated in the fixing means.

As a further improvement of the invention, the fixing means can be designed as a one-piece cylindrical inflatable component with retaining clips formed onto its outer perimeter.

An embodiment of the invention is explained in greater detail below with reference to the figures.

DESCRIPTION OF THE PREFERRED EMBODIMENTS

Figure 1:
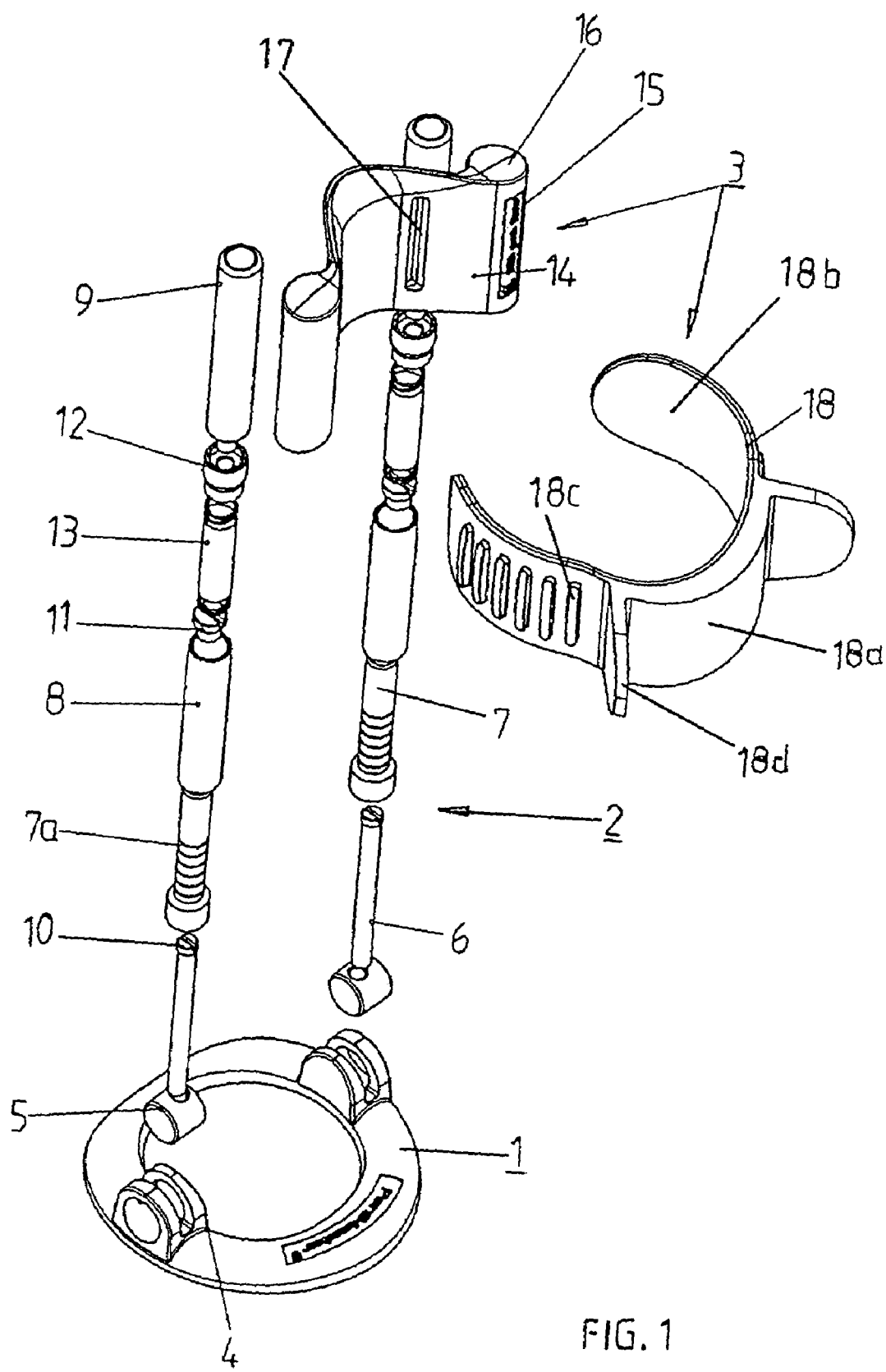
FIG. 1 shows a perspective exploded view of the device according to the invention for permanent penis expansion.
Figure 2:
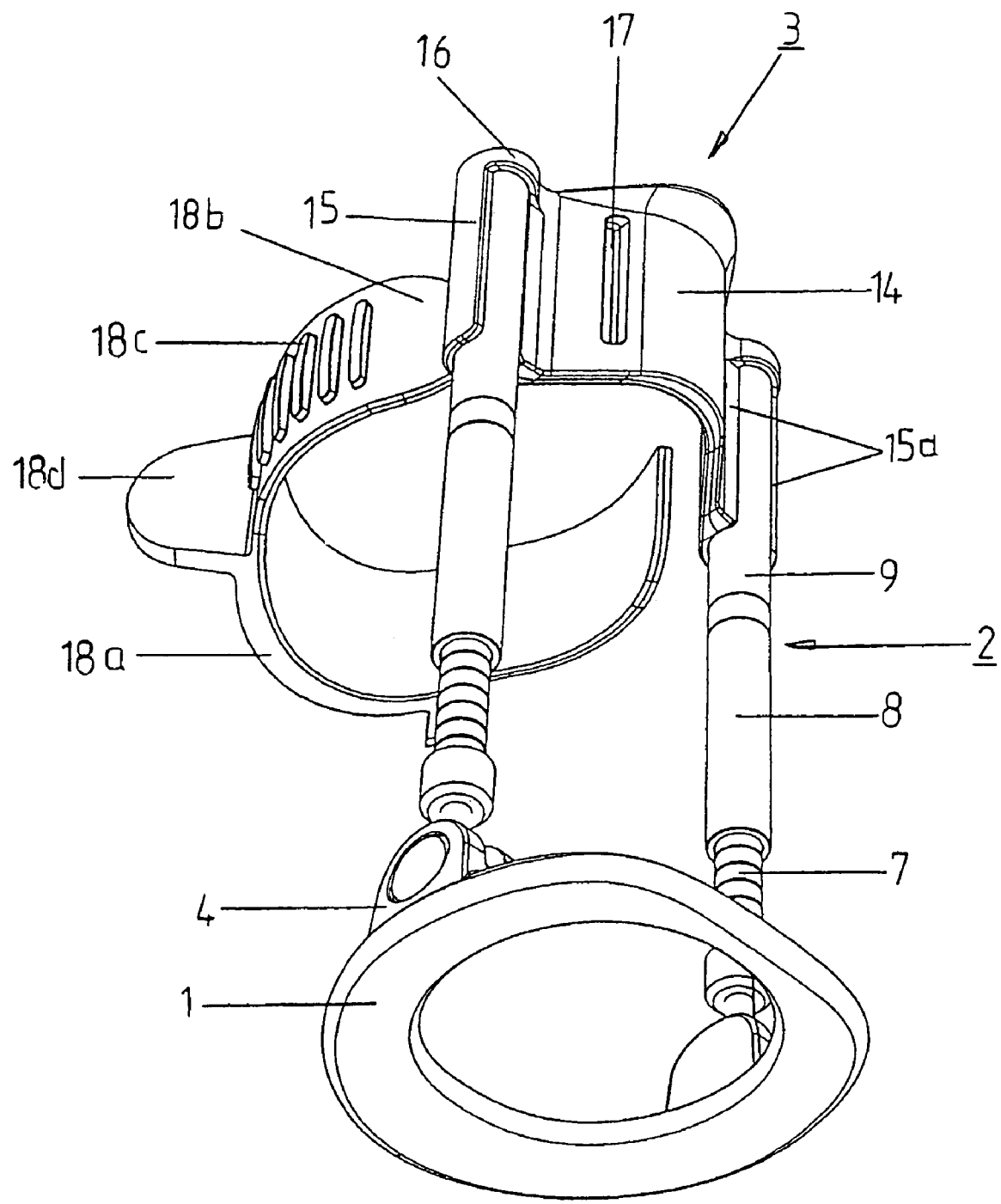
FIG. 2 shows a perspective rear view of the device according to FIG. 1 in assembled condition.

As is visible in the figure, the device comprises a support ring 1 for providing support on the user's body, two parallel pivoted stretching rods 2 that can be extended gradually and are flexible in axial direction, and a detachable fixing means 3 at the distal ends of the two stretching rods 2 for gripping and fixing the penis in the glans region. Two articulated receptacles 4 for receiving a jointed piece 5 that can be pivoted around a horizontal axis are formed on opposite sides onto the front surface of the support ring 1. The rear of the support ring 1 is an even closed surface with a rounded transition into the front surface. The stretching rod 2 consists of a threaded rod 6 that is connected to the joint piece 5, an adjustment bush 7 that can be adjusted in axial direction as it is connected to the stretching rod 2 via a female thread, a spring cover 8 that is telescopically arranged on the adjustment bush 7 and spring-loaded towards the distal end of the stretching rod 2, and one or several extension rods 9. The peripheral surface of the adjustment bush 7 comprises markings 7a that indicate the size of the tensile force applied by the spring cover 8 in accordance with the position of said spring cover 8 on the adjustment bush 7. The threaded rod 6 comprises a stop piece 10 that can be screwed onto its end that prevents the adjustment bush 7 from unintentional release from the threaded rod 6 during extension. The spring cover 8 that is held when pulled out by a stop piece 11 screwed to the front of the adjustment bush 7 and closed by a locking adapter 12, contains a spring 13 that presses the spring cover 8 toward the distal end of the stretching rod 2. The locking adapter 12 can be screwed onto extension rod 9. The two-part fixing means 3 of the embodiment shown consists of a substantially rigid receiving shell 14 that has a concave shape in the support surface area and retaining clips 15 formed onto its sides that comprise a cylindrical plug-in part 16. The upper rim of the receiving shell 14 is bent towards the rear of the receiving shell. The receiving shell 14 can be attached from the side to the stretching rods 2 using the retaining clips 15 that have the form of a cylinder slotted in longitudinal direction with flexible cheeks 15a, while the plug-in part 16 allows provides locking in longitudinal direction. The receiving shell 14 comprises slots 17. The second part of the fixing means 3 consists of a rubber-elastic fastening element 18 comprising a flexible supporting part 18a that is domed according to the shape of a penis and has very rounded edges, two fastening straps 18b with latches 18c formed onto them at a spacing for locking the fastening straps 18b in the slots 17 of the receiving shell 14, and two shackles 18d acting in opposite direction of the fastening straps 18b for releasing the fastening element 18 and limiting the tension forces. The user can conveniently put on the fixing means designed in this way so that injuries or painful pinching are excluded. Painless fastening is mainly promoted by the flexible and the preformed and rounded design of the supporting part 18a. The shackles 18d prevent application of too much tension force and facilitate fast and convenient release of the fastening element 18. After putting on the fixing means 3, the retaining clips 15 are locked sideways into the stretching rods 2 that were put on before and are supported against the body using the support ring 1. The cylindrical plug-in part 16 provides security in addition to lateral locking. An upper limiting plate on the retaining clip 15 is sufficient to prevent the fixing means 3 from slipping down.

Figure 3:
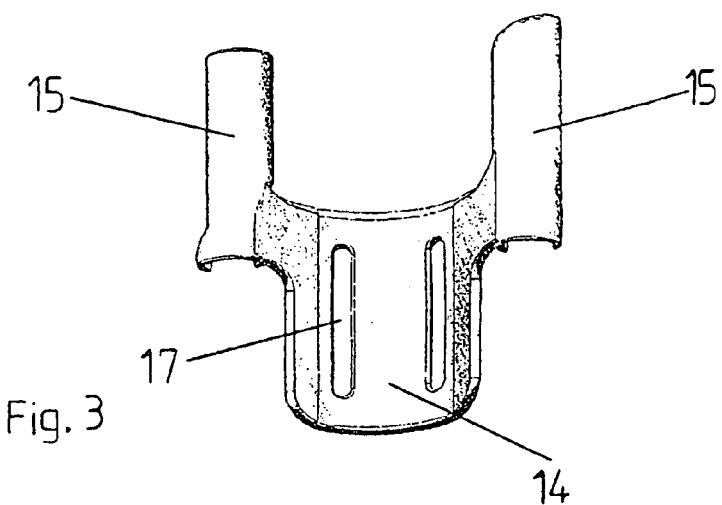
FIG. 3 shows a perspective view of an embodiment of the receiving shell with retaining clips offset towards the top in stretching direction and extending beyond the receiving shell.

According to a preferred embodiment shown in FIG. 3, the retaining clips 15 are formed onto the upper rim of the receiving shell 14. This makes it possible, after putting on the fixing means, to connect the retaining clips 15 and the stretching rods without overstretching even a very short penis. The retaining clips that protrude upwards at the same time protect the upper exposed part of the penis. The slots 17 in the receiving shell 14 can be of oblong design in order to vary the attachment of the elastic fastening element 18 in the stretching direction.

According to another embodiment not shown in the figure, the fastening element 18 can be designed as a flexible and inflatable strap or hose-type hollow body whose ends are connected to the receiving shell 14 or detachably held thereon. After putting on the fixing means 3 of such design with the inflatable fastening element in uninflated condition, air is blown into the inflatable fastening element using an external pump or a pump integrated in the fixing means or a compressed air cartridge to gently fasten the penis without any risk of pinching. In an improvement of this embodiment, the receiving shell 14 can be an inflatable hollow body or the entire fixing means 3 can be designed as a double-walled cylindrical hollow body with diametrically opposed retaining clips 15 on its outer wall. The outer wall can be rigid and the inner wall flexible. Both walls can be flexible as well. After inflating the double-walled cylindrical fixing means with at least a flexible inner wall, the inner diameter is reduced and the inner wall evenly and flexibly tightens along the entire perimeter of the penis. In yet another variant not shown in the figure, an elastic bulge surrounding the fixing means fully or partially can be attached to the distal rim of the respective fixing means to optimize fastening in axial direction.

Figure 4:
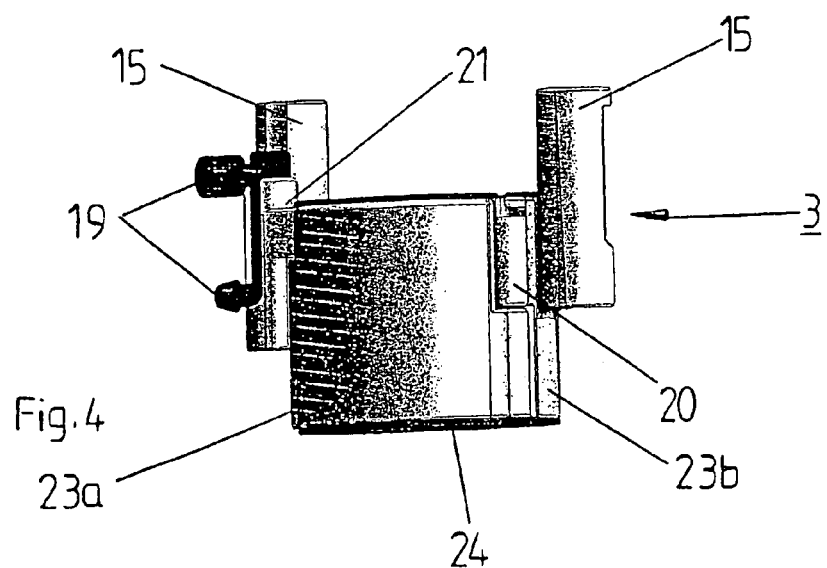
FIG. 4 shows a view of a cylindrical folding fixing means with air cushioned inner surfaces and offset retaining clips.
Figure 5:
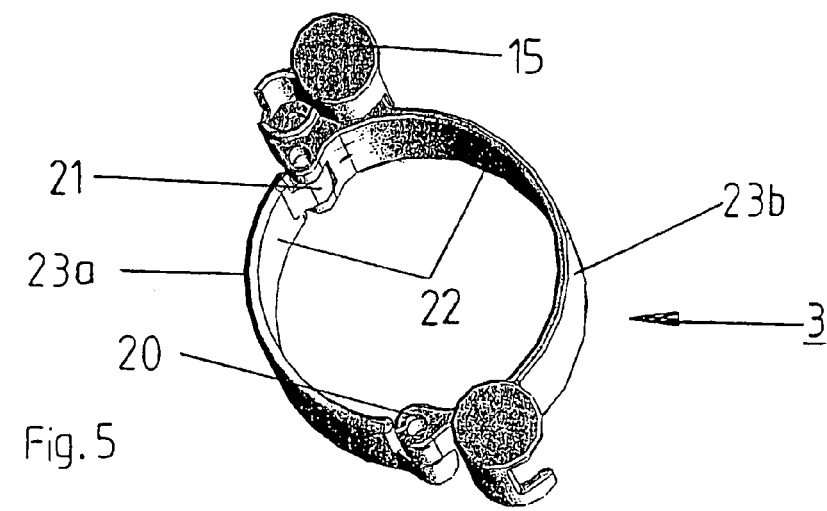
FIG. 5 shows a top view of the fixing means according to claim 4 with an elastic foam lining.

A preferred embodiment of a substantially circular, cylindrical fixing means 3 that fully and flexibly surrounds the penis, with retaining clips 15 offset in stretching direction, is shown in FIGS. 4 and 5. The fixing means 3 in this embodiment consists of two shells 23a, 23b connected by a hinge 20 and a lock 21. In the embodiment according to FIG. 4, an inflatable air cushion ring 24 split in the area of the lock 21 and equipped with valves 19 on its outside to supply and discharge air is attached to the inner surfaces of shells 23a, 23b. According to the variant shown in FIG. 5, an elastic gel or foam lining 22 is applied to the inner surfaces of the two rigid shells 23a, 23b and broken in the lock section so that the upper shell 23a can completely be swiveled away from the lower shell 23b. Shells 23a, 23b differ in size, and the retaining clips 15 are attached at an upward offset in stretching direction to the bigger shell 23b. The lock 21 can be of an adjustable design such as a locking, snap fastener, or velcro system so that the inner perimeter of the fixing means can be adjusted to the perimeter of the penis, achieving safe and gentle fastening. The air cushion ring 24 can be inflated using an external electric or manual air pump, a compressed air cartridge, or respiratory air.

What is claimed is:

1. A device for extending the penis, comprising a support ring, at least one stretching rod coupled to a proximal end of the support ring and spring-mounted in an axial direction that can gradually be adjusted in length, and fixing means retained on a distal end of the at least one stretching rod, wherein the fixing means is a substantially cylindrical preformed component that fully or partially and flexibly surrounds the penis and is provided with at least one retaining clip running in a longitudinal direction on an outer rim of the fixing means and locking sideways into the at least one stretching rod after putting on the fixing means, and wherein said at least one retaining clip is designed as a continuously slotted cylinder with flexible cheeks and a distal stop plate.

2. The device according to claim 1, wherein the at least one retaining clip extends from the distal section of the fixing means in a stretching direction and beyond its distal end.

3. The device according to claim 1, wherein the fixing means consists of a concave receiving shell with at least one retaining clip extending from its sides at the distal end and an elastic fastening element.

4. The device according to claim 3, wherein the fastening element consists of a domed preformed flexible support part from the ends of which extend elastic fastening straps, the outer surfaces of said fastening straps comprising latches for locking the fastening straps into slots of the receiving shell and shackles for releasing the fastening straps and for limiting tension forces.

5. The device according to claim 4, wherein the latches and slots have rounded edges.

6. The device according to claim 4, wherein the thickness of the domed support part is multiple times greater than that of the elastic fastening straps.

7. The device according to claim 4, wherein the fastening element can be adjusted in the longitudinal direction by variably fixing it to the receiving shell, the length of the slots exceeding the width of the fastening strap.

8. The device according to claim 1, wherein the cylindrical fixing means consists of two shells connected by a hinge and a lock and forming a cylinder, and in that a highly elastic material is applied to the inner surfaces of said shells.

9. The device according to claim 8, wherein said highly elastic material is an inflatable air cushion ring that is split in the section of the lock.

10. The device according to claim 9, wherein an inlet and outlet valve is located in the wall of the air cushion ring and in that the inflatable part is inflated using an external pump or compressed air cartridge or a manual pump or compressed air cartridge integrated in the fixing means.

11. The device according to claim 8, wherein said highly elastic material is a foam or gel.

12. The device according to claim 8, wherein the two shells differ in size and in that the retaining clips are attached to the bigger shell.

13. The device according to claim 8, wherein the lock can be adjusted for setting the size of the inner diameter formed by the two shells.

14. The device according to claim 13, wherein the adjustable lock is a locking, snap fastener, or hook and loop fastener.

15. The device according to claim 1, wherein the fixing means is designed as a one-piece cylindrical, double-walled, inflatable component with a flexible inner wall and a flexible or rigid outer wall and at least one retaining clip mounted to the outer wall, said component comprising an inlet and outlet valve for inflating and deflating air.

16. The device according to claim 1, wherein the at least one stretching rod is attached to the support ring using a ball joint and in that the at least one retaining clip is coupled to the fixing means.

17. The device according to claim 1, wherein the at least one stretching rod for elastic change in length consists of a threaded rod, an adjustment bush screwed to it, and a spring-mounted spring cover telescopically encompasses the adjustment bush, and in that the distal end of the threaded rod comprises a stop piece to prevent complete unscrewing of the adjustment bush.

18. The device according to claim 17, wherein markings are provided around the perimeter of the adjustment bush to indicate the tensile force generated by the spring cover.

19. The device according to claim 17, wherein the at least one stretching rod can be combined of multiple extension rods screwed together at various lengths.

* * * * *